United States Patent [19]

Secor

[11] 4,216,329
[45] Aug. 5, 1980

[54] METHOD OF PRODUCING γ-AMINO ALCOHOLS
[75] Inventor: Henry V. Secor, Midlothian, Va.
[73] Assignee: Philip Morris Incorporated, New York, N.Y.
[21] Appl. No.: 590,669
[22] Filed: Jun. 26, 1975
[51] Int. Cl.$^2$ .................... C07D 213/38; C07C 85/08
[52] U.S. Cl. ............................ 546/334; 260/566 AE; 260/570.6; 260/584 R
[58] Field of Search ............ 260/296 R, 584 R, 570.6, 260/566 AE; 546/334

[56] References Cited
U.S. PATENT DOCUMENTS

| | | | |
|---|---|---|---|
| 2,832,804 | 4/1958 | Richter et al. | 260/566 AE |
| 3,198,833 | 8/1965 | Beregi et al. | 260/566 AE |
| 3,845,126 | 10/1974 | Giraudon et al. | 260/566 AE |
| 3,904,689 | 9/1975 | Ashby | 260/566 AE |
| 3,914,300 | 10/1975 | Haddock et al. | 260/566 AE |

OTHER PUBLICATIONS

Ginsburg "Concerning Amines", (1967), p. 42.
Houben–Weyl "Metider Org. Chemie", vol. 11/1 (1957), p. 510.
Morrison et al. "Organic Chemistry", 2nd ed. (1966), pp. 636 and 683.
Wiley "Five and Six Membered Compounds with Nitrogen and Oxygen", (1962), pp. 118, 119, 122, 123, 126, 127.

Primary Examiner—Henry R. Jiles
Assistant Examiner—R. W. Ramsuer

[57] ABSTRACT

A process for the production of γ-amino alcohols from β-dicarbonyl compounds is disclosed. The dicarbonyls are reacted with alkoxyamines and the resultant alkoximino compounds reduced to yield γ-amino alcohols. Also described are novel substituted γ-amino alcohols.

5 Claims, No Drawings

METHOD OF PRODUCING γ-AMINO ALCOHOLS

BACKGROUND OF THE INVENTION

γ-amino alcohols have been prepared by sequences including reaction of ammonia or amines with substituted acrylic acids or esters to give the corresponding β-amino acid or ester. These β-amino acids were then reduced to yield the γ-amino alcohol.

Such a sequence has substantial drawbacks. The initial reaction with ammonia or amine is often complicated by competing side reactions such as amide formation. Additionally, this reaction, and particularly the final reduction step, are seriously affected by the presence of substituents on the intermediates. Consequently, many desirable products have been available only in very minor and difficult to isolate amounts, while others could not be produced at all.

It has long been desired to obtain an alternative route for the synthesis of γ-amino alcohols. Further, it has been desired to obtain a means for producing γ-amino alcohols bearing substituents on one or more of the α, β, or γ positions.

These, and other objects and advantages as are described below, have been achieved pursuant to the present invention.

DESCRIPTION OF THE INVENTION

The present invention relates to the production of γ-amino alcohols by a novel synthesis route. More particularly, it has been discovered that β-dicarbonyl compounds such as β-diketones, β-ketoesters, and α-formyl derivatives of esters, ketones and aldehydes may be converted into their corresponding γ-amino alcohols.

The present starting materials for the synthesis of γ-amino alcohols comprise compounds within the scope of either of the following two formulae:

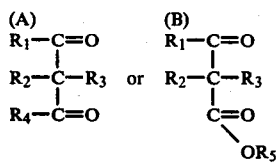

Wherein:
R$_1$ is hydrogen, alkyl, aryl, or alkylaryl; each of R$_2$ and R$_3$ is hydrogen, alkyl, aryl, alkylaryl, heteroaromatic, or alkylheteroaromatic;
R$_4$ is hydrogen, alkyl, aryl, or alkylaryl; and
R$_5$ is alkyl.

As utilized herein in description of the present invention, alkyl means an alkyl group of from 1 to 10 carbons, preferably methyl or ethyl. Aryl means an aromatic such as phenyl, tolyl, chlorophenyl, or naphthyl. Alkylaryl means a group such as benzyl. Heteroaromatic means pyridyl, furanyl, or the like. By alkylheteroaromatic, it is meant the analogs of the alkylaromatics such as picolyl.

In referring to aromatic ring configurations, substituents are not excluded. The degree of substitution permitted includes alkyl, cycloalkyl, aryl, arylalkyl, heteroaromatic, alkylheteroaromatic and halogen at any of the available carbons of the ring. Acid addition salts of heteroaromatics and alkylheteroaromatics, such as the hydrochloride, are also included.

In accordance with this invention, the β-dicarbonyl starting material is reacted with an alkoxyamine, preferably methoxyamine, ethoxyamine or benzyloxyamine to produce the corresponding β-alkoximino product. This reaction proceeds readily. Ordinarily, it is performed in an appropriate solvent, such as methanol, at room temperature or above. The alkoxyamine and β-dicarbonyl should ordinarily be provided in an essentially equal molar ratio. This helps to ensure the production of the monoalkoximino intermediate.

Under most circumstances, no difficulty is encountered in producing the monoalkoximino intermediate. The reaction with alkoxyamine at one of the two molecular carbonyl groups is ordinarily selective. Consequently, a yield of at least about 80% is normally obtained. Where one of the carbonyl groups is an ester, the formation of alkoximino occurs exclusively at the other carbonyl group. Consequently, an essentially quantitative conversion to the monoalkoximino intermediate is then possible.

Once the monoalkoximino compound has been produced, it is reduced to obtain a γ-amino alcohol of the present invention. This reduction may be achieved with almost any strong reducing agent. Particularly preferred such agents, however, are the mixed metal hydrides. Thus, for example, LiAlH$_4$, NaAlH$_2$—(OCH$_2$CH$_2$OCH$_3$)$_2$ or a similar reducing agent may be employed.

As is customary with such a reduction, the reaction should occur in a suitable solvent, such as dimethoxyethane. Where sensitive substituents, such as heteroaromatics are present, the reaction is preferably performed at low temperature. Thus temperatures below about 20°, most preferably from about −10° to +5° C., are preferred. At least 3 to 5 days are ordinarily required for completion of this reaction. Where only stable substituents such as alkyl and aryl are present, however, higher temperatures up to about 100° C. are permitted. These higher temperatures significantly shorten the reaction time to as little as 1 to 2 hours.

After reduction, the γ-amino alcohol may be isolated. This is ordinarily accomplished by dispersing the reaction mixture in an immiscible aqueous-organic solvent system. The organic phase may then be separated and the solvent distilled to yield the product, γ-amino alcohol.

Certain of the compounds produced in accordance with the present invention are old in the art. Thus, for example, many such compounds exhibit known pharmacological activities. Descriptions of these compounds and their utilities may be found in U.S. Pat. No. 2,151,517 of Kamlet; Japanese Patent No. 14,788 (1963); and "Tremor-Producing Aminopropanols" by Horner et al, published in the *Journal of Medicinal Chemistry*, 10, 387–391 (1967).

The products of this invention are also valuable as intermediates in the preparation of azetidine compounds. Such azetidine compounds have been shown to possess pharmacological activity as adrenergics, ganglionics, to be anti-flammatory, anti-convulsant, and monoaminoxidase inhibitory. A desirable means of converting γ-amino alcohols to these azetidines is disclosed in U.S. Application No. 590,670 (abandoned) of Edwards et al entitled "Azetidine Compounds And Process For Production" and was filed on the same date as this application.

Certain of the products of the present reaction sequence are, however, novel. These amino alcohols are ones having the formula:

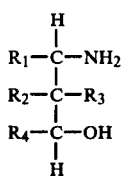

Wherein:
R₁ is hydrogen, alkyl, aryl or alkylaryl; each of R₂ and R₃ is hydrogen, alkyl, aryl, alkylaryl, heteroaromatic or alkylheteroaromatic;
R₄ is hydrogen, alkyl, aryl, or alkylaryl; and
at least one of R₂ and R₃ is heteroaromatic or alkylheteroaromatic.

Particularly preferred novel compounds are those in which α-, β-, and/or γ-substituents which are alkyl have from 1 to 5 carbons. Similarly, preferred aryl and alkylaryl groups are phenyl, tolyl and benzyl, whereas the preferred heteroaromatics are pyridyl and furanyl and the preferred alkyheteroaromatic is picolyl. In these novel compounds, at least one of R₂ and R₃ must be a heteroaromatic, preferably one in which the heteroatom is nitrogen. Most preferred are compounds of the foregoing formula in which one of R₂ or R₃ is pyridyl.

These aromatic groups may be bonded to the amino alcohol at any available ring position. In the case of pyridyl, however, the 3-pyridyl group is preferred. Similarly, these aryl, alkylaryl, heteroaromatic and alkylheteroaromatics may contain various ring substituents as were previously identified. Thus, for example, the available ring valences may be satisfied by hydrogen, halogen, alkyl, aryl, alkylaryl, heteroaromatic or alkylheteroaromatic constituents. Also, addition salts of, for example, heteroaromatics and alkyl heteroaromatics are included.

As previously indicated, many γ-amino alcohols having α-, β-, or γ-substituents could not be produced by the synthesis routes of the prior art. The present sequence of steps for the first time makes these γ-amino alcohol derivatives available by production from the correspondingly substituted β-dicarbonyl derivatives.

These novel compounds of the present invention generally exhibit the same utilities as have already been known for such compounds in the prior art. They have also proven valuable for the synthesis of azetidine compounds by the method set forth in the previously identified application of William B. Edwards, III and Henry V. Secor. Accordingly, such application is incorporated by reference herein, further to disclose additional utilities and uses for the products of the present invention.

The present invention will be more apparent from the following examples which were chosen from among the many specific combinations possible. They are intended to illustrate this invention and are not limitative of its scope.

EXAMPLE 1

36.8 g of sodium bicarbonate were agitated with 36.2 g of methoxyamine hydrochloride in 1.5 liters of methanol until gas evolution ceases. The mixture was cooled to 5° and 81.8 g of ethyl 2-formyl-2-(3-pyridyl)acetate were added. After stirring for twelve hours at room temperature, the mixture was concentrated to a small volume under reduced pressure and the residue distributed between water and methylene chloride. The organic phase was washed with saturated sodium bicarbonate, water and saturated sodium chloride. Distillation then yielded 74.0 g (78.5%) of ethyl 2-(3-pyridyl)-3-methoximinopropionate, b.p. 114°-116°/0.15 mm.

Over a 2.5 hour period 22.65 g of the ethyl 2-(3-pyridyl)-3-methoximinopropionate were added to a slurry of 17.45 g of lithium aluminum hydride in one liter of dimethoxyethane. The temperature was maintained at from −5° to 0° C. After 5 days at room temperature, the mixture was cooled to 0° and slowly combined with 85 ml of saturated sodium chloride solution. After 4 hours, the mixture was filtered and concentrated at reduced pressure.

The oily residue was dried by azeotroping with benzene and ethanol. After concentration, 11.50 g (74%) of crude 3-amino-2-(3-pyridyl)-1-propanol was obtained as a viscous yellow oil.

The I.R. spectra was compatible with the structure and confirmation was confirmed by reaction with p-toluenesulfonyl chloride in pyridine to give the O,N-ditosylate derivative, i.e., 2-(3-pyridyl)-3-p-toluenesulfonamidopropyl p-toluenesulfonate, m.p. 170°-170.5° C.

EXAMPLE 2

A mixture of 3.09 g of ethoxyamine hydrochloride, 60 ml of pyridine and 6.0 g of ethyl benzoylacetate was stirred and heated 85° C. for 18 hours. The solvent was then removed under reduced pressure and the residue distributed between methylene chloride and water. The methylene chloride phase was then dried and distilled at reduced pressure to obtain 5.5 g (75%) of ethyl 3-phenyl-3-ethoximinopropionate.

A slurry of 512 mg of lithium aluminum hydride was combined with 1.0 g of the ethoximino ester in 25 ml of dimethoxyethane. After heating under reflux for 2 hours, the mixture was cooled to 0° and 2.5 ml of saturated NaCl were added. After stirring overnight at room temperature, the mixture was filtered and concentrated under reduced pressure and the resulting oil taken up in methylene chloride and dried with MgSO₄. The solvent was evaporated and recrystallizing the resulting solid from benzene petroleum ether yielded 540 mg (74%) of 3-phenyl-3-amino-1-propanol, m.p. 72°-3°.

EXAMPLE 3

Commercially available hydrocinnamic acid was converted to its ethyl ester. This ester was then reacted with ethyl formate in the presence of a sodium-potassium alloy as set forth in *Bull. Soc. Chim. France*, 895–899 (1951) to produce ethyl α-formyl hydrocinnamate.

The ethyl α-formyl hydrocinnamate (6.0 g, 29.1 mmole) was added to a magnetically stirred solution of dry pyridine (60 ml) containing methoxyamine hydrochloride (2.49 g, 29.8 mmole). The resultant solution was heated at 70° for 18 hours, concentrated in vacuo and the residue distributed between water and methylene chloride. The organic phase was washed with water, dried and concentrated to afford 6.73 g (90%) of ethyl 2-benzyl-3-methoximinopropionate.

This intermediate (1.0 g, 4.25 mmole) was added to a slurry of dry 1,2-dimethoxyethane (50 ml) containing lithium aluminum hydride (482 mg, 12.75 mmole). It was then heated under reflux for 1.5 hours, cooled to 0°, treated with saturated sodium chloride (2.5 ml) and then heated at 60° for 1 hour. The mixture was filtered, concentrated and the residue redissolved in methylene chloride and dried with sodium sulfate. Filtration and concentrate gave 680 mg of crude 2-benzyl-3-amino-1-propanol. A 316 mg sample of the amino alcohol was treated with 173 mg of oxalic acid in 3 ml absolute ethanol to give the pure crystilline oxalate, m.p. 149°–150° (rep. 150°-2° CA, 41, 13167 g). Ir, nmr and Raman analysis were compatible with the correct structure.

EXAMPLE 4

Using the process of Example 3, 3-amino-2-phenyl-1-propanol was prepared by reducing the reaction product of methoxyamine and ethyl 2-formyl-2-phenylacetate. The 3-amino-2-phenyl-1-propanol was recovered as a yellow oil. Upon conversion to the hydrochloride, it exhibited a melting pt. of 119°–120° C.

Anal. Calculated for $C_9H_{14}NOCl$: C, 57.60; H, 7.52; N, 7.46; Cl, 18.89; Found: C, 57.39; H, 7.50, N, 7.51; Cl, 18.60.

I claim:

1. A process for the production of γ-amino alcohols comprising reacting a β-dicarbonyl compound having one of the formulae:

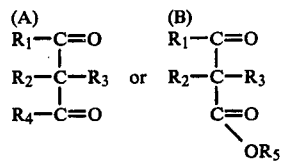

wherein:
$R_1$ is hydrogen, alkyl, aryl or alkylaryl; each of $R_2$ and $R_3$ is hydrogen, alkyl, aryl, alkylaryl, heteroaromatic, or alkylheteroaromatic;
$R_4$ is hydrogen, alkyl, aryl, or alkylaryl; and $R_5$ is alkyl;
with alkoxyamine selected from the group consisting of methoxyamine, ethoxyamine or benzyloxyamine to produce the monoalkoximino intermediate and reducing said intermediate to yield γ-amino alcohol.

2. The process of claim 1, wherein both $R_2$ and $R_3$ are hydrogen.

3. The process of claim 1, wherein one of $R_2$ and $R_3$ is a heteroaromatic or alkyl heteroaromatic.

4. The process of claim 3, wherein $R_2$ is pyridyl and $R_3$ is hydrogen.

5. The process of claim 1, wherein the monoalkoximino intermediate is reduced with lithium aluminum hydride.

* * * * *

UNITED STATES PATENT AND TRADEMARK OFFICE
CERTIFICATE OF CORRECTION

PATENT NO. : 4,216,329
DATED : August 5, 1980
INVENTOR(S) : Henry V. Secor

It is certified that error appears in the above-identified patent and that said Letters Patent are hereby corrected as shown below:

Column 4, line 60, "(90%)" should read --(99%)--.

Signed and Sealed this

Sixth Day of January 1981

[SEAL]

Attest:

SIDNEY A. DIAMOND

*Attesting Officer*    *Commissioner of Patents and Trademarks*